(12) United States Patent
Morgan

(10) Patent No.: US 11,266,623 B2
(45) Date of Patent: Mar. 8, 2022

(54) USE OF CANNABINOIDS AND TERPENES FOR TREATMENT OF ORGANOPHOSPHATE AND CARBAMATE TOXICITY

(71) Applicant: KOTZKER CONSULTING LLC, Yardley, PA (US)

(72) Inventor: Joseph Morgan, Yardley, PA (US)

(73) Assignee: Kotzker Consulting LLC, Yardley, PA (US)

(*) Notice: Subject to any disclaimer, the term of this patent is extended or adjusted under 35 U.S.C. 154(b) by 56 days.

(21) Appl. No.: 16/004,004

(22) Filed: Jun. 8, 2018

(65) Prior Publication Data
US 2018/0311205 A1 Nov. 1, 2018

Related U.S. Application Data

(63) Continuation of application No. 14/649,951, filed as application No. PCT/US2013/076223 on Dec. 18, 2013, now abandoned.

(60) Provisional application No. 61/738,782, filed on Dec. 18, 2012.

(51) Int. Cl.
| | |
|---|---|
| *A61K 31/352* | (2006.01) |
| *A61K 31/045* | (2006.01) |
| *A61K 31/015* | (2006.01) |
| *A61K 31/05* | (2006.01) |
| *A61K 31/5517* | (2006.01) |
| *A61K 31/5513* | (2006.01) |
| *C07D 451/10* | (2006.01) |
| *A61K 45/06* | (2006.01) |
| *A61K 31/01* | (2006.01) |
| *A61K 31/4425* | (2006.01) |
| *A61K 31/46* | (2006.01) |
| *C07D 471/08* | (2006.01) |

(52) U.S. Cl.
CPC ............ *A61K 31/352* (2013.01); *A61K 31/01* (2013.01); *A61K 31/015* (2013.01); *A61K 31/045* (2013.01); *A61K 31/05* (2013.01); *A61K 31/4425* (2013.01); *A61K 31/46* (2013.01); *A61K 31/5513* (2013.01); *A61K 31/5517* (2013.01); *A61K 45/06* (2013.01); *C07D 451/10* (2013.01); *C07D 471/08* (2013.01)

(58) Field of Classification Search
CPC .... A61K 31/352; A61K 31/05; A61K 31/662; A61K 31/325
See application file for complete search history.

(56) References Cited

U.S. PATENT DOCUMENTS

| | | | |
|---|---|---|---|
| 6,096,740 A | 8/2000 | Mechoulam et al. | |
| 6,211,230 B1 | 4/2001 | Filbert et al. | |
| 6,369,052 B1 | 4/2002 | Kellar et al. | |
| 6,630,507 B1 | 10/2003 | Hampson et al. | |
| 6,946,150 B2 | 9/2005 | Whittle | |
| 7,105,685 B2 | 9/2006 | Travis | |
| 7,109,245 B2 | 9/2006 | Kunos et al. | |
| 7,709,536 B2 | 5/2010 | Whittle | |
| 8,034,843 B2 | 10/2011 | Whittle et al. | |
| 8,211,946 B2 | 7/2012 | Whittle | |
| 8,603,515 B2 | 12/2013 | Whittle | |
| 8,642,645 B2 | 2/2014 | Kelly | |
| 8,673,368 B2 | 3/2014 | Guy | |
| 8,790,719 B2 | 7/2014 | Parolaro et al. | |
| 9,035,130 B2 | 5/2015 | Meijer | |
| 9,125,854 B2 | 9/2015 | Bottje et al. | |
| 9,205,063 B2 | 12/2015 | Guy et al. | |
| 9,675,579 B2 | 6/2017 | Rock et al. | |
| 9,956,182 B2 | 5/2018 | Yeshurun | |
| 2005/0126562 A1* | 6/2005 | Rabinowitz | A61M 15/0051 128/200.23 |
| 2007/0112017 A1* | 5/2007 | Barlow | A61K 31/137 514/282 |
| 2010/0016418 A1 | 1/2010 | Guy | |
| 2010/0286098 A1* | 11/2010 | Robson | A61P 1/00 514/161 |
| 2011/0117184 A1 | 5/2011 | Bromley et al. | |
| 2011/0257256 A1 | 10/2011 | Fuchs et al. | |
| 2012/0059062 A1 | 3/2012 | Whittle | |
| 2012/0231083 A1 | 9/2012 | Carley et al. | |
| 2012/0295968 A1 | 11/2012 | Kelley et al. | |
| 2014/0243405 A1 | 8/2014 | Whalley | |
| 2015/0086653 A1 | 3/2015 | Parolaro et al. | |

FOREIGN PATENT DOCUMENTS

| | | |
|---|---|---|
| GB | 2478595 | 9/2011 |
| WO | 2007/148094 A1 | 12/2007 |
| WO | 2009/147439 A1 | 12/2009 |

(Continued)

OTHER PUBLICATIONS

Pertwee; "Emerging strategies for exploiting cannabinoid receptor agonists as medicines"; 2009; British Journal of Pharmacology; 156: 397-411 (Year: 2009).*

Chang et al., "Protective Effect of [beta]-Caryophyllene, a Natural Bicyclic Sesquiterpene, Against Cerebral Ischemic Injury," Journal of Medicinal Food (2013), 16(6): 471-480.

Guimaraes-Santos et al., "Copaiba Oil-Resin Treatment Is Neuroprotective and Reduces Neutrophil Recruitment and Microglia Activation after Motor Cortex Excitotoxic Injury," Evidence-Based Complementary and Alternative Medicine (2012), 2012:1-9.

Department of the Airforce, "USAF Operations in a Chemical and Biological (CB) Warfare Environment, CB Hazards" Airforce Handbook 32-4014 (1997) vol. 2.

(Continued)

*Primary Examiner* — Timothy P Thomas
(74) *Attorney, Agent, or Firm* — Fox Rothschild LLP

(57) ABSTRACT

Pharmaceutical compositions in which isolated cannabinoid receptor modulators are optionally combined with terpene blends in a pharmaceutically acceptable carrier. Methods for treating or preventing a disease, disorder, dysfunction or condition caused by exposure to an organophosphate or carbamate acetylcholinesterase inhibitor with the inventive compositions are also disclosed.

18 Claims, 2 Drawing Sheets

(56) References Cited

FOREIGN PATENT DOCUMENTS

| WO | 2009147439 | 12/2009 |
|---|---|---|
| WO | 2011110866 | 9/2011 |

OTHER PUBLICATIONS

Kim et al., "Destruction and Detection of Chemical Warfare Agents," Chem. Rev. 2011, 111, 5345-5403.
Seierstad and Breitenbucher, Discovery and Development of Fatty Acid Amide Hydrolase (FAAH) Inhibitors, American Chemical Society (2008), 51(23): 7327-7343.
Musilek et al., "Chapter 18: Progress in Antidotes (Acetylcholinesterase Reactivators) Against Organophosphorus Pesticides," Pesticides in the Modern World—Effects of Pesticides Exposure (Edited by Margarita Stoytecheva) 2011: 341-358.
Borger, J., "Marijuana substitute combats nerve gas" Scripps Howard News Service (Jan. 5, 1998), Retrieved from http://www.mapinc.org/drugnews/v98/n417/a14.html.
Burstein SH, Friderichs E, Kogel .B, Schneider J, Selve N. "Analgesic effects of 1í, 1í dimethylheptyl-delta8-THC-11-oic acid (CT3) in mice." Life Sci 1998;63:161-68. reviewed in Mechoulam 2001).
"Canadian Consortium for the Investigation of Cannabinoids in Human Therapeutics (CCIC)," Submission to the Senate Committee on Illegal Drugs (Jun. 11, 2001).
Chagas, Marcos Hortes N., José Alexandre S. Crippa, Antonio Waldo Zuardi, Jaime EC Hallak, João Paulo Machado-de-Sousa, Camila Hirotsu, Lucas Maia, Sergio Tufik, and Monica Levy Andersen. "Effects of acute systemic administration of cannabidiol on sleep-wake cycle in rats." Journal of Psychopharmacology 27, No. 3 (2013): 312-316.
Dunn et al., "Pretreatment for nerve agent exposure," Chapter 6, Medical Aspects of Chemical and Biological Warfare, [1997] Textbook of Military Medicine, Published by the Office of the Surgeon General, Borden Institute, Walter Reed Army Medical Center Washington,D.C. Office of The Surgeon General United States Army, pp. 181-196.
Filbert et al., "Neuroprotective effects of HU-211 on brain damage resulting from soman-induced seizures," Annals New York Academy of Sciences (2006), Neuroprotective Agents: Fourth International Conference (1999) 890(1):504-514.
Gallily, Ruth, Zhannah Yekhtin, and Lumír Onděj Hanuš. "Overcoming the bell-shaped dose-response of cannabidiol by using cannabis extract enriched in cannabidiol." Pharmacol Pharm 6 (2015): 75-85.
Gillert, D., "Pentagon projects more judicious use of nerve agent drug," American Forces Press Service (Oct. 20, 1999), Retrieved from http://ojc.org/NL/nov99/nerveagent.html.
Hiltunen, A. J., and T. U. C. Järbe. "Interactions between Δ9-tetrahydrocannabinol and cannabidiol as evaluated by drug discrimination procedures in rats and pigeons." Neuropharmacology 25, No. 2 (1986): 133-142.
Lake et al., "Cannabinoid-Induced Hypotension and Bradycardia in Rats is Mediated by CB1-Like Cannabinoid Receptors," JPET (1997), 281(3): 1030-1037.
Mechoulam R, Hanus L, "The cannabinoids an overview: Therapeutic implications in vomiting and nausea after cancer chemotherapy, in appetite promotion, in multiple sclerosis and in neuroprotection," Pain Res Manag (2001) 6(2): 67-73.
Nava et al, "Inhibition of hippocampal acetylcholine release after acute and repeated Δ9-tetrahydrocannabinol in rats" Brain Research (1998), 809:1-4 1998.
Nava et al., "D2 dopamine receptors enable Δ9-tetrahydrocannabinol induced memory impairment and reduction of hippocampal extracellular acetylcholine concentration," Br J Pharmacol (2000) 130: 1201-1210.
Walker JM, Strangman NM, Huang SM, "Cannabinoids and Pain," Pain Res Manag, (2001) 6(2): 74-78.
Wright, M. Jerry, Sophia A. Vandewater, and Michael A. Taffe. "Cannabidiol attenuates deficits of visuospatial associative memory induced by Δ9tetrahydrocannabinol." British journal of pharmacology 170, No. 7 (2013): 1365-1373.
Albuquerque et al. (2006) "Effective countermeasure against poisoning by organophosphorus insecticides and nerve agents," PNAS 103(35): 13220-13225.
Aracava et al. (2009), "Effectiveness of Donepezil, Rivastigmine, and (+/−) Huperzine A in Counteracting the Acute Toxicity of Organophosphorus Nerve Agents: Comparison with Galantamine," The Journal of Pharmacology and Experimental Therapeutics, 331(2): 1014-1024.
Blair et al., (2015), "Cannabinoids: is there a potential treatment role in epilepsy," Expert Opin Pharmacother. 13(13): 1911-1914.
Carlini et al., (1974) "Effects of Marihuana in Laboratory Animals and in Man," Br. J. Pharmac. 50: 299-309.
Chang et al. (2007), "Quantitative structure-activity relationship (QSAR) for neuroprotective activity of terpenoids", Life Sciences, Pergamon Press: Oxford, GB, 80 (9): 835-841.
Cilio et al., (2014) "The case for assessing cannabidiol in epilepsy," Epilepsia, 55(6): 787-790.
Eyer et al. (2009). "Obidoxime in acute organophosphate poisoning: 1-clinical effectiveness," Clincal Toxicology 47:798-809.
Filbert et al. (1999), "Neuroprotective Effects of HU-211 on Brain Damage Resulting from Soman-Induced Seizures," Annals of New York Academy of Sciences, 890:505-514.
Fischedick et al. (2010), "Cannabinoid Receptor 1 Binding Activity and Quantative Analysis of Cannabis sativa L. Smoke and Vapor," Chem. Pharm. Bull. 58 (2): 201-207.
Hill et al. (2012), "Cannabidivarin is anticonvulsant in mouse and rate." British Journal of Pharmacology, 167: 1629-1642.
Horst Theirmann et al. (2009), "Comments on Efficacy of two new asymmetric bispyridinium oximes (K-27-K-48) in rats exposed to diisopropylflurophosphate: Comparison with pralidoxime, obidoxime, trimedoxime, methoxime, and HI 6," Toxicology Mechanisms and Methods, 19 (4): 334-334.
Jones et al. (2010), "Cannabidiol Displays Antiepileptiform and Antiseizure Properties in Vitro and in Vivo," The Journal of Pharmacology and Experimental Therapeutics, 332 (2): 569-577.
Jun et al. (2009), "Commercially available antidotes of organophosphate poisonings (pralidoxime, obidozime, methozime, trimedoxime and HI-6) and newly developed oxime K027 as reactivators of human acetylcholinesterase nhibited by selected organophosphate pesticides," Toxicology Letters 189S:S217 Abstract.
Kurtz, P.H. (1990) "Pralidoxime in the Treatment of Carbamate Intoxication," American Journal of Emergency Medicine 8(1): 68-70.
Maa et al. (2014) "The case of medical marijunana in epilepsy," Epilepsia 55(6): 783-786.
Maccarrone et al., (2002), "Estrogen stimulated arachindonolyethanolamide release from human endothelial cells and platelet activation," Blood 100:4040-4048.
Nallapaneni et al., (2006) "Modulation of paraoxon toxicity by the cannabinoid receptor agonist WIN 55, 212-2," Toxicology, 227: 173-183; Nallapaneni et al., (2008) "Pharmacological enhancement of endocannabinoid signaling reduces the cholinergic toxicity of diisopropylfluorophosphate," NeuroToxicology, 29:1037-1043.
Nallapaneni et al., (2008) "Pharmacological enhancement of endocannabinoid signaling reduces the cholinergic toxicity of diisopropylfluorophosphate," NeuroToxicology, 29:1037-1043.
Newmark (2005): "Nerve Agents," Neurologic Clinics, Elsevier Science, US 23(2) 623-641.
Sadri et al. (2010) "Cannabinoid Receptor Agonist WIN-55,212-2 Protects Differentiated PC12 Cells from Organophosphorus Induced Apoptosis," International Journal of Toxicology 29(2): 201-208.
Schultz et al.,(2016) "JZL 195 Which Increases Endocannabinoids, Reduces Soman-Induced Status Epilepticus, Hyperactivity, and Brain Damage in Rats," Cannabinoid Studies at MRICD: 2 pgs.
Thabet H et al. (2006) "Comparative study of two dosage regimens of pralidoxime in human organophosphate poisonings," 164: 122.
Wright et al., (2010) "Behavorial sequelae following acute diisopropylfluorophosphate intoxication in rats: Comparative affects of atropine and cannabinomimetics," Neurotoxicology and Teratology 32:329-335.

(56) References Cited

OTHER PUBLICATIONS

See Balali-Mood et al., "Recent Advances in the Treatment of Organophosphorous Poisonings"; Iran J. Med. Sci., Jun. 2012; 37(2): 74-91.

\* cited by examiner

| Terpenes | mg/g |
|---|---|
| α-Bisabolol | <LLOQ |
| Borneol | <LLOQ |
| Camphene | 0.11 |
| Campher | 0.01 |
| Δ3-Carene | 0.01 |
| β-Caryophyllene | 1.85 |
| Caryophyllene oxide | <LLOQ |
| α-Cedrene | 0.00 |
| β-Eudesmol | <LLOQ |
| (+) Fenchol | <LLOQ |
| Geraniol | <LLOQ |
| Guaiol | <LLOQ |
| α-Humulene | 0.17 |
| Isoborneal | 0.01 |
| Limonene | 3.56 |
| Linalool | 2.50 |
| Menthol | <LLOQ |
| Myrcene | 3.31 |
| Nerol | 0 |
| cis-Ocimene | <LLOQ |
| trans-Ocimene | <LLOQ |
| α-Phellanderene | 0.16 |
| α-Pinene | 8.40 |
| β-Pinene | 0.04 |
| Sabinene Hydrate | 0.00 |
| α-Terpinene | <LLOQ |
| α-terpineol | 0.00 |
| Terpinolene | 0.01 |
| α-Guaiene (t) | <LLOQ |
| Elemene (t) | <LLOQ |
| Farnesene (t) | 0.01 |
| Germacrene B (t) | <LLOQ |
| Guaia-1(10) 11-diene (t) | <LLOQ |
| t-2-Pinanol (t) | 0.00 |
| Selina-3 7(11)-diene (t) | <LLOQ |
| Eudesm-7(11)-en-4-ol (t) | <LLOQ |
| Valencene (t) | <LLOQ |
| Sum of Terpenes | 20.15 |

USE OF CANNABINOIDS AND TERPENES FOR TREATMENT OF ORGANOPHOSPHATE AND CARBAMATE TOXICITY

CROSS REFERENCE TO RELATED APPLICATIONS

This application is a continuation of U.S. patent application Ser. No. 14/649,951 filed on Jun. 5, 2015, which is a continuation of International Application Ser. No. PCT/US2013/076223 filed on Dec. 18, 2013, which claims priority to U.S. Provisional Application Ser. No. 61/738,782, filed Dec. 18, 2012, the disclosures of which are incorporated herein by reference in their entireties.

FIELD OF THE INVENTION

The present invention discloses the novel uses of cannabinoid system modulators and terpenes in treatment of the symptoms and signs of anticholinesterase toxicity associated with organophosphate ("OP") and/or carbamate exposure. More particularly, the present invention relates to compositions containing cannabinoid receptor agonists and derivatives thereof, including partial agonists and modifiers of cannabinoid metabolism and terpenes for prevention and treatment of acute and chronic OP toxicity and acute and chronic carbamate toxicity.

BACKGROUND OF THE INVENTION

Organophosphates are compounds having the general chemical formula:

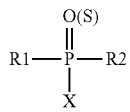

wherein R1 and R2 are alkyl-, alkoxy-, alkylthio- or amido groups and X is an acyl residue or leaving group when the OP phosphorolates acetylcholinesterase (AChE). The R groups are generally esters, amides, or thiol derivatives of phosphoric, phosphonic, or phosphinic acids. In an OP, the O or (S) has a double bond with the central P. If the S is present the compound is a phosphorothioate but is still called an OP because of its mechanisms of action. Phosphorothioates must be biotransformed to an oxon, with an O replacing the S, to become an OP. An example of such includes the biotransformation of parathion to paraoxon. Without the replacement of the S with an O, there is no inhibition of AChE. OP inhibition of AChE is initially reversible but may become irreversible based on binding time.

Carbamates are carbamic acid derivatives and reversibly inhibit AChE having the general formula:

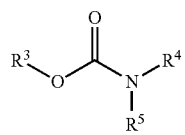

Carbamate insecticides include aldicarb (Temik), carbofuran (Furadan), carbartk (Sevin), methyl carbamate, ethienocarb, and others. Carbamate esters are also caused urethanes. OPs typically cause a more severe and difficult to treat cholinergic crisis because OPs are capable of irreversibly inhibiting AChE.

OP and carbamate compounds are typically used as insecticides, pesticides, petroleum additives, and petrochemicals. Deadly OPs and carbamates have also been developed for use as chemical warfare nerve agents by conventional armies, military special forces, desperate regimes, and/or terrorists. Sarin, a highly potent OP, was used by Sadam Hussain's Republic of Iraq against Kurdish civilians in Halabja and other villages in March 1988 killing at least 3200 people and injuring many more people. (These attacks also involved two other OPs, Vx and tabun and mustard gas). The 1995 Tokyo subway attacks by a "religious "cult" used the same OP injuring many civilians. The use of Sarin more than once recently in the Syrian conflict lead to many casualties alarming the international community about the risks to the stability of the region.

Monocrotophos was the OP insecticide responsible for killing 23 school children in India who ate contaminated food, in a widely publicized incident. At least 750,000 cases of OP poisoning occur every year. Mortality and morbidity is higher in poorer countries where OP and carbamate pesticides, some of which are banned in developed countries, are inexpensive and accessible. They are estimated to cause around 300,000 fatalities a year. See Balali-Mood et al, "Recent Advances in the Treatment of Organophosphorous Poisonings"; Iran J. Med. Sci., 2012 June; 37(2): 74-91. Pharmacologically, OPs behave as anticholinesterase agents inhibiting the acetylcholinesterases (AChEs) enzymes and other esterases resulting in increased cholinergic tone. In summary, OP and carbamate pesticides cause hundreds of thousands of deaths each year and many more injuries.

AChE is a serine protease in the carboxylesterase family of enzymes with EC number 3.1.1.7. Mammals have a single AChE gene; however, AChE diversity in humans results from location, other molecular associations such as with membrane components, as well as from alternative mRNA splicing and posttranslational associations or structural and catalytic subunits. Inhibition of AChE prevents the breaking down of the neurotransmitter ACh thereby increasing both the level and duration of action of this neurotransmitter. ACh is a neurotransmitter that contributes to nerve conduction following its release in the central nervous system (CNS) as well as autonomic ganglia at sympathetic preganglionic synapses, at parasympathetic postganglionic synapses, and at neuromuscular junctions.

At the skeletal neuromuscular junction the ACh receptor is nicotinic. In the autonomic nervous system the ACh receptor is muscarinic. Both muscarinic and nicotinic ACh receptors are found in the central and peripheral nervous system. AChE catalyzes the hydrolysis of the acetylcholine into choline and acetic acid. Such a reaction is necessary to allow a cholinergic neuron to return to its resting state after activation to restore normal muscle and neurological activities. AChEs are very efficient with each functional enzyme capable of hydrolyzing at least 5000 ACh hydrolytic reactions per second. DFP or diisopropylfluorophosphate is an OP developed in 1941. DFP bears structural similarity or homology with the nerve agent sarin. DFP has activity similar to sarin, although DFP is less potent. DFP is commonly used as a research OP proxy for sarin. See generally Goodman & Gillman, The Pharmacological Basis of Therapeutics 10th edition, 2001, Chapter 7 and Handbook of Toxicology of Chemical Warfare Agents, edited by Ramesh Gupta, 2009, especially chapters 6, 7, 32, 33, 42, 43, 61, 63, and 64.

The effects of chronic and acute exposure to OP and carbamates have been extensively documented in the literature. When OPs or carbamates are used as insecticides the prolonged exposure and inhalation of such compounds could lead to multiple ophthalmic and neuromuscular symptoms. OPs are also used as warfare nerve agents, ("nerve gas") and acute exposure to them by any route of exposure can be fatal. Carbamates may also be used in war or in terrorist attacks. Even if not fatal, exposure may lead to temporary incapacitation as well as permanent cognitive deficits, depression and other neuropsychiatric disorders. Current treatment after acute injury does not seem to prevent the emergence of "Organophosphate induced delayed neuropathy," an axonopathy. In any event, OP and carbamate casualties require medical intervention and decontamination.

Nerve agents, also called gasses regardless of physical state, are classified by the US military and into two types of agents, the G- and the V-class agents. G-agents such as tabun (GA) and sarin (GB) were originally synthesized by a German group during the 1930s and except for tabun (GA; ethyl N,N-dimethylphophoramidocyanidate) include fluorinated compounds of organophosphate, such as sarin (GB; 2-fluoromethyl-phophoryloxypropane), soman (GD; 3-fluoro-methyl-phosphoryloxy-2,2-dimethyl-butane), and cyclosarin (GF; fluoro-methyl-phophoryloxycyclohexane). G agents are volatile liquids at room temperature with a slightly higher density than water. Their primary route of entry is via the respiratory tract and mucous membranes such as the eye. Because of their high volatility G agents are considered non persistent nerve agents. Toxic exposures are most likely to be via eye, mouth, nose, and especially involve the respiratory tract unless filtered and/or neutralized by an improvised or purposely built gas mask. G agents in liquid form may penetrate skin and as well as volatilize presenting significant respiratory hazards. The respiratory tract tissues, primarily the air sacs or alveoli, provide a large surface area, about 100 square meters. The skin surface area in about 1.73 square meters. Loss of consciousness is expected in less than one minute with death expected in less than 15 minutes following 2 deep breaths of highly concentrated G class vapors. Since G agents and some OP pesticides are colorless, tasteless, and virtually odorless, they may also be accidently ingested into the GI tract or ingested via deliberate contamination of food and drinking liquids.

V-agents were initially synthesized after World War II by scientists from the United Kingdom. The V agents are sulfur containing organophosphate compounds including VE (S-2-diethylamino ethyl O-ethylethylphophonothioate), VG (2 diethoxyphosphorylsulfanyl-N,N-diethyletanamine), VM (2-ethoxy-methylphosphoryl sulfanyl-N,N-diethylethanamine), VR or RVX (Russian VX; N,N-diethyl-2-methyl-2-methylpropoxy phosphoryl sulfanylethanamine) and VX (S-2 diisopropylamino O-ethylmethylphosphonothioate). The V-agents, oily liquids at room temperature that very slowly release gas due to their low volatilities, are both more toxic, as well as longer persisting in the environment than the G-agents. Their primary, but not the sole route of entry, is via skin contact. A single drop of VX the size of this dot (.) unless rapidly decontaminated or removed, may be fatal within 30 minutes if placed on intact thin moist skin, faster if on a wound, and within 120 minutes if on dry thick skin. The human LD 50 for VX is 10 mg.

Toxicity associated with OP compounds mainly results from excessive cholinergic stimulation through inhibition of AChE. The resulting hypercholinergic tone crisis may also cause other neuronal hyperexcitation, e.g., glutamate release and depletion of high energy phosphates leading to cellular damage and physiological exhaustion. Nerve agents react rapidly with a serine hydroxyl group in the active site of AChE to form a phosphate or phosphonate ester. Phosphorylated AChE is not able to functionally hydrolyze ACh. Functional ACh regenerates very slowly. Thus, the enzyme will remain inhibited until new enzyme is generated, or until an enzyme re-activator (oxime) is used, as long as receptor aging or irreversible binding from molecular rearrangements of the AChE from the effect of the OP has yet not occurred.

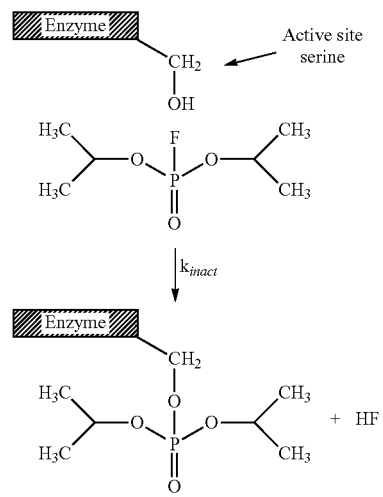

As depicted in the schematic above, AChE represented by the Enzyme, contains serine in the active (esteratic) site. Following the binding of DFP to this site the AChE is inactivated. This inactivation of AChE may be hydrolyzed slowly and spontaneously or rapidly reversed or restored with an oxime (and perhaps other chemicals). However, the binding or inhibition can eventually become permanent (irreversible or aged).

The symptoms of OP and carbamate toxicity are receptor and body site specific. Nerve agents antagonize muscarinic receptors to cause miosis, ocular ciliary or pupillary constrictor muscle spasm and eye pain, glandular hypersecretion (salivary, bronchial, lacrimal/tear glands), bronchoconstriction, vomiting, diarrhea, urinary and fecal incontinence, and bradycardia.

Nerve agents act on nicotinic receptors to cause sweating, hypertension, tachycardia, and on skeletal muscle, they cause initial fasiculations, twitching, tremors, spreading areas of spasm, and defasciculation from exhaustion followed by weakness and flaccid paralysis.

Nerve agents also antagonize cholinergic receptors to produce irritability, giddiness, fatigue, lethargy, amnesia, ataxia, seizures, coma, respiratory depression, and paralysis. Nerve agents independently cause cardiac tachycardia and hypertension via stimulation of the adrenal medulla. Exposure to low concentrations of nerve agent vapor further produce immediate ocular symptoms, including rhinorrhea (from nasolacrimal duct drainage), and in some patients, even dyspnea. These ocular effects are secondary to the localized absorption of vapor across the outermost layers of the eye, causing lacrimal gland stimulation (tearing), pupillary sphincter contraction (miosis), and ciliary body spasm (ocular pain).

As the exposure increases, dyspnea and gastrointestinal symptoms ensue. Intoxication signs and symptoms and treatment of patients exhibiting OP or carbamate toxicity is similar. Retrospective data review series involving OP and carbamate toxicity are frequently combined. See for example the 46 patient 5-year review from Jordan, a country where OP and carbamate agricultural insecticides are widely used. These chemicals are also used as agents in suicides and to injure enemies. See A M Saadeh et al, "Cardiac manifestations of acute carbamate and organophosphate poisoning" Heart, 1997; 77:461-464.

It is well documented that exposure to high concentrations of nerve agent vapor causes immediate loss of consciousness, followed shortly by convulsions, flaccid paralysis, and respiratory failure. These generalized effects are caused by the rapid absorption of nerve agent vapor across the respiratory tract, producing maximal inhibition of AChE within seconds to minutes of exposure. Nerve agent vapor exposure, unless aggressively treated and to include decontamination to prevent reexposure to patient and also endanger rescuer, is expected to have significant effects by the time victims present to the emergency care system. Decontaminants include soap and water as well as the more effective expedient dilute chlorine bleach solutions for skin, dilute baking soda (sodium bicarbonate) solutions for eyes, nostrils, hair, ears, mouth, and other delicate tissues and genitourinary mucous membranes, or RSDL. RSDL is Reactive Skin Decontamination Lotion, a specialty pharmaceutical topical product issued to combat soldiers and some first responders. RSDL achieves a much more rapid and effective decontamination than any of the expedients.

The effect of dermal exposure from liquid nerve agent depends on the anatomic site exposed, ambient temperature, and dose of nerve agent. Percutaneous absorption of nerve agent typically results in localized sweating caused by direct nicotinic effect on the skin, followed by muscular fasciculations and weakness as the agent penetrates deeper and a nicotinic effect is exerted on underlying muscle. Following moderate dermal exposures, vomiting and/or diarrhea occur. Vomiting and/or diarrhea soon after exposure are ominous signs. With further absorption, full-blown systemic or remote effects occur. Nerve agents cause death via respiratory failure, which in turn is caused by increased airway resistance (e.g., bronchospasm), excessive bronchopulmonary secretions, respiratory muscle paralysis, and most importantly, loss of central respiratory drive.

Other studies have shown that nerve gases such as sarin produced delayed and long-term effects on cardiac function such as reduced ejection fraction. Sarin caused left ventricular dilation two months after an asymptomatic dose. This is a marker for dilated cardiomyopathy. Levels of atrial and brain natriuretic peptides in the heart were increased, indicating cardiac remodeling possibly due to volume overload. It has also been reported that prolonged exposure to OP leads to cognitive impairment of central information processing leading eventually to IQ loss. See Davis et al, Advances in Psychiatric Treatment, 2000; 6: 187-192.

The treatment modalities generally depend on severity of intoxication. In addition to decontamination, there are several treatments for intoxicated patients. More specifically, such treatments include administration of intravenous or intramuscular atropine, at least 2 mg at a time for adults, to counteract muscarinic over-stimulation, and an intravenous or intramuscular oxime, typically pralidoxime or 2-PAM, to reactivate acetyl cholinesterase. For example, the US military uses as front line therapy autoinjectors for IM administration combining 2.1 mg of atropine with 600 mg of 2-PAM. If fasciculation or seizures are present, the US military, prior to arrival of a medic, uses as a GABA A anti-seizure agent IM diazepam 10 mg in an autoinjector. Soldiers are given kits containing 3 autoinjectors of the combination atropine/pralidoxime and 3 autoinjectors containing diazepam 10 mg. There is no ceiling on the dose of atropine: additional injections are titrated vs adverse symptoms other than miosis every few minutes as needed. In other countries, armed forces and/or emergency protocols use a different oxime, e.g., obidoxime or HI6, a different antimuscarinic (anticholinergic), e.g., scopolamine and/or other belladonna alkaloids in place of atropine, and a different anti-seizure agent, e.g., avizafone or midazolam or barbiturates. For some patients the dose of atropine required may exceed 100 mg! In the absence of OP intoxication an atropine dose of 2 mg will cause severe poisoning and a dose of 100 mg will be fatal. For this reason, Israel stopped including atropine with its gas mask kits for civilians after severe adverse reactions to atropine happened in civilians who injected atropine in response to sirens warning of incoming SCUD missiles during the first Gulf War in 1991.

Supportive and intensive care therapy includes the use of oxygen, IV fluids, glucose, and electrolytes (salts) and bicarbonate, to replace the fluids and salts and bicarbonate lost from vomiting, diarrhea, profuse sweating (diaphoresis) and respiratory secretions. In addition, titrated IM and IV diazepam to control convulsions, atropine/oxime, mechanical respiration, and intensive cardiorespiratory and neurological sign monitoring with aggressive treatment of cardiac rhythm disorders and pulmonary edema. Experimental cholinesterase infusions are also being researched as are catalytic scavengers that would split an OP molecule to render it inactive, such as from infusions of FFP or Fresh Frozen Plasma, or from stoichiometric scavengers to bind an OP and antibodies against OPs. Recent investigations have revealed that intravenous infusion of sodium bicarbonate to produce mild to moderate alkalinization is effective. Gacyclidine, an antiglutamatergic compound, was also proved to be beneficial in conjunction with atropine, pralidoxime, and diazepam in nerve agent poisoning. Intravenous magnesium sulfate was reported to decrease hospitalization duration and improved outcomes in patients with organophosphorous poisoning from pesticides. Ketamine may also be useful if given early. See Balali-Mood et al, Iran J Med Sci. 2012 June; 37(2): 74-91.

At present, pyrostigimine bromide 30 mg tablets (PB) every 8 hours seems to be the most common prophylactic. PB is approved for military medical use by the US FDA at this dose and frequency for this indication for soman. G-agent soman ages the AChE in under 2 minutes. Soman is probably the most rapidly aging OP (based on non-classified or public domain data). Pre-exposure treatment with PB sequesters some AChE from OP binding and aging. Any subsequent post OP or post carbamate intoxication is more rapidly and more effectively treated with atropine/oxime therapy. Like all medications PB has adverse effects. Adverse reactions to PB include salivation, lacrimation, urination, defecation symptoms and miosis. Prophylactic use of PB has also been linked to the Gulf War Syndrome. Regimens used by trained soldiers acting under military medical orders in other countries include prophylactic tablets with physostigmine rather than pyridostigmine with or without Trihexyphenidyl, benactyzine, and/or a transdermal patch containing HI-6.

Access to effective prophylaxis and treatment has important implications for military or civilian populations since low-dose, non-symptomatic exposure to OPs or carbamates may result in long-lasting effects. See Fusek et al, Curr. Med. Chem. 2009; 16(23):2977-86 and Chapter 63, Prophylactic and Therapeutic Measures in Nerve Agent Poisoning in Handbook of Toxicology of Chemical Warfare Agents, edited by Ramesh Gupta, 2009, and US Prescribing Information for Physostigmine bromide 30 mg for military medical use.

However, since pyridostigmine barely crosses the blood-brain barrier it provides no protection against nerve agent-induced central injury. Pyridostigmine, as written in the FDA approved prescribing information, is ineffective when administered without post-exposure treatment of atropine/2 PAM or similar drugs. Also many of the prophylactic and treatment regimens cause cognitive impairment or excessive dryness (e.g., atropine and other antimuscarinics), certainly not desirable in combat situations or hot environments where perspiration also serves as a temperature regulator. Excessive dryness increases the chances of heat exhaustion related disorders including heat stroke.

Therefore, other directions for different types of prophylactic and non-injection, less expensive, and self-administered treatments (or those not requiring an intensive care unit for potentially therapy) should be explored. Atropine overdose or misuse risks heat stroke and temporary psychosis. A common mnemonic used to describe the physiologic manifestations of atropine overdose is: "hot as a hare, blind as a bat (from very dilated pupils and cycloplegia), dry as a bone, red as a beet, and mad as a hatter". These associations reflect the specific changes of warm, dry skin from decreased sweating, blurry vision with hypersensitivity to light, decreased sweating/lacrimation, vasodilation, and central nervous system effects on muscarinic receptors, type 4 and type 5. This set of symptoms is known as anticholinergic toxidrome.

Recently there have been discussions on combination prophylactic therapies including such compounds as carbamates (reversible AChE inhibitors) and central anticholinergics or NMDA receptor antagonists, benzodiazepines or partial agonists for benzodiazepine receptor, and other central AChE inhibitors. The transdermal route is an alternative way for delivering the prophylactic agent and has also been discussed in the art. Regardless, there is still a need for additional prophylactic or adjunct to existing prophylactic regimens to mitigate drug related adverse events or direct treatments to alleviate undesired symptoms associated with the OP and carbamate toxicities. There is a need particularly for nontoxic treatment modalities, with favorable therapeutic indices compared with PB, atropine and such respiratory depression-inducing anticonvulsants as midazolam, diazepam, and barbiturates. There is a need for anti OP and carbamate therapy that may be easily self-administered or easily administered by first responder medics and paramedics in mass casualty situations or even by lightly injured casualties to each other and to more seriously injured casualties. In the event of mixed nerve agent/conventional warfare casualties, there is also a need for antidotes to the nerve agents that won't have significant drug/drug interactions with medications used to treat surgical wounds including general anesthesia agents. The present invention addresses such shortcomings.

SUMMARY OF THE INVENTION

The present invention discloses the role of cannabinoids in mitigating OP toxicity via manipulation of the endocannabinoid (EC) system and other physiological systems.

In one embodiment, the present invention discloses a pharmaceutical composition comprising an isolated cannabinoid receptor modulator, and optionally containing a blend of terpenes in a pharmaceutically acceptable carrier.

In another embodiment, the present invention discloses a pharmaceutical composition further comprising a blend of two or more terpenes selected from the group consisting of limonene, pinene, myrcene, linalool, beta caryophylene, terpineol, and terpinolene.

In another embodiment of the invention, the terpene blend comprises two or more terpenes selected from the group consisting of limonene, pinene, myrcene, linalool, and beta caryophylene.

In another embodiment of the invention, the weight ratio of said terpenes is in range of about 1-10:about 1-10:about 1-6:about 1-6:0.25-3, respectively.

In another embodiment of the invention, the weight ratio of said terpenes is about 4:4:3:3:1 respectively.

In another embodiment of the invention, the weight ratio of said terpenes is about 4:7:3:3:1 respectively.

Another embodiment of the present invention discloses a pharmaceutical composition, wherein said cannabinoid receptor modulator agonist is a CB receptor agonist or a modifier selected from the group consisting of phytocannabinoids, tetrahydrocannabinol (THC), (−)-trans-delta-9-THC, dronabinol, (±)-trans-3-(1,1-dimethylheptyl)-6,6a,7,8,10,10a-hexahydro-1-hydroxy-6,6-dimethyl-9H-dibenzo[b,d]pyran-9-one (nabilone), anandamide, 2-arachidonoyl-glycerol (2-AG), N-acyl-phosphatidylethanolamine-phospholipase D, diacyl glycerol lipase (DAGL), cannabidiol (CBD), abnormal cannabidiol (abn-CBD), nabiximols, EPIDIOLEX®, rimonabant, (−)-1,1-dimethylheptyl analogs of 11-hydroxy-8-tetrahydrocannabinol (HU210), HU 211, HU 308, ajulemic acid, AM-411, L-759, 633, AM-855, VCHSR, nonabine, JWH 133, JWH-171, BML-190, A-41988, O-806, O-2694, O-2545, JZL184, JWH-359, CB-13, GW-405,833, JTE-907, URB754, inhibitors of FAAH or fatty acid amide hydrolasel-(methylpiperidin-2-ylmethyl)-3-(2-iodo-5-nitrobenzoyl)indole (AM-1241), WIN 55,212-2, other natural or endogenous endocannabinoid derivatives, and combinations thereof.

The pharmaceutical composition of the present invention is in oral, nasal, topical, ophthalmic, buccal, sublingual, rectal, vaporization-ready, nebulization-ready, nanoparticle formulations, liposomal formulations, vaginal and/or IV or other parenteral form.

The pharmaceutical composition of the present invention further comprises one or more non-cannabinoid active ingredients selected from the group consisting of a terpene, a benzodiazepine, a belladonna alkaloid, an anticholinesterase, an oxime, and combinations thereof.

In an embodiment of the invention, belladonna alkaloid is atropine and anticholinesterase is pyridostigamine.

Another embodiment of the invention is directed to a method of treating or preventing a disease, disorder, dysfunction, or syndrome caused by exposure to an organophosphate (OP) or carbamate acetylcholinesterase inhibitor, said method comprising administering to a subject exposed to or at risk of exposure to said OP or carbamate a pharmaceutical composition of the present invention in an amount effective to modulate the cannabinoid receptors of said subject.

In an embodiment of the invention, the pharmaceutical composition is for treating disease, disorder, dysfunction, or syndrome selected from the group consisting of muscle disorder, ophthalmic dysfunction, metabolic disorders, cardiac, rhythm and contractility dysfunctions, social related disorders, mood disorders, seizures, learning disorders, cognition disorders, memory disorders, respiratory disorders, locomotor activity disorders, movement disorders, immune disorders, inflammation, cell growth, pain or neurodegenerative related syndromes, drug abuse, alcohol abuse, bipolar disorder, cognitive impairment, post-traumatic stress disorder (PTSD), Gulf War like syndrome, and premature senile dementia.

In one embodiment of the invention, the muscle disorder is selected from the group consisting of dyskinesia, akinesia, tremor, bradykinesia, and skeletal muscle rigidity and spasticity.

In one embodiment of the invention, the ophthalmic disorder is selected from the group consisting of miosis, ciliary muscle spasm, ophthalmic pain, headache, and lacrimation disorder.

In another embodiment of the invention, the OP is a G or V class nerve agent.

In another embodiment of the invention, the cannabinoid receptor modulator is selected from the group consisting of phytocannabinoids, tetrahydrocannabinol (THC), (−)-trans-delta-9-THC, dronabinol, (±)-trans-3-(1,1-dimethylheptyl)-6,6a,7,8,10,10a-hexahydro-1-hydroxy-6,6-dimethyl-9H-dibenzo[b,d]pyran-9-one (nabilone), anandamide, 2-arachidonoyl-glycerol (2-AG), N-acyl-phosphatidylethanolamine-phospholipase D, diacyl glycerol lipase (DAGL), cannabidiol (CBD), abnormal cannabidiol (abn-CBD), nabiximols, EPIDIOLEX®, rimonabant, (−)-1,1 dimethylheptyl analogs of 11-hydroxy-8-tetrahydrocannabinol (HU 210), HU 211, HU 308, ajulemic acid, AM-411, L-759,633, AM-855, VCHSR, nonabine, JWH 133, JWH-171, BML-190, A-41988, O-806, O-2694 and O-2545, JZL184, JWH-359, CB-13, GW-405,833, JTE-907, URB754, inhibitors of FAAH or fatty acid amide hydrolasel-(methylpiperidin-2-ylmethyl)-3-(2-iodo-5-nitrobenzoyl)indole (AM-1241), WIN 55,212-2, other natural or endogenous endocannabinoid derivatives, and combinations thereof.

Another embodiment of the invention provides for administering a non-cannabinoid receptor modulator selected from the group consisting of opioids, gabapentins, pregabalins, benzodiazepines, atropines, oximes, antioxidants, alkalizing agents, terpenes, and NSAIDs.

Another embodiment of the invention provides for administering the composition in oral, nasal, topical, ophthalmic, buccal, sublingual, rectal, vaporization-ready, nebulization-ready, nanoparticle formulations, liposomal formulations, vaginal and/or IV or other parenteral form.

Another embodiment of the invention provides for administering the composition prior to exposure to said organophosphate or carbamate and said composition comprises at least one terpene selected from the group consisting of limonene, mycrene, pinene, linalool, beta caryophyllene, and a cannabinoid selected from the group consisting of THC, CBD, and a mixture of THC and CBD.

Another embodiment of the invention provides for the step of exposing said subject to an OP or carbamate acetylcholinesterase inhibitor as a prophylactic treatment.

Another embodiment of the invention provides for administering to a subject atropine and an oxime in an amount effective to prevent adverse effects from said prophylactic exposure to OP or carbamate.

Another embodiment of the invention provides for co-administering pyridostigmine bromide to a subject.

Another embodiment of the invention provides for administering to said subject after exposure to an OP or a carbamate acetylcholinesterase inhibitor and said composition comprises a blend of CBD and THC in a weight ratio of between about 3 and 400 mg to about 0.0001 and 10 mg, respectively.

Another embodiment of the invention provides for administering a blend of two or more terpenes.

In another embodiment of the invention the terpine blend comprises two or more terpenes selected from the group consisting of limonene, pinene, myrcene, linalool, beta caryophylene, terpineol, and terpinolene.

Another embodiment of the invention provides for a method of treating or preventing a disease, disorder, dysfunction, or syndrome caused by exposure to an organophosphate or carbamate acetylcholinesterase inhibitor, said method comprising administering to a subject exposed to or at risk of exposure to said OP or carbamate a composition comprising at least two terpenes selected from the group consisting of limonene, myrcene, linalool, beta caryophylene, terpineol, terpinolene, and pinene, in an amount effective to treat or prevent said disease, disorder, dysfunction, or syndrome.

Another embodiment provides for a terpene mixture comprises alpha pinene.

Another embodiment provides a blend which comprises beta-caryophylene, limonene, myrcene, and linalool.

Another embodiment provides a compound having the following structure:

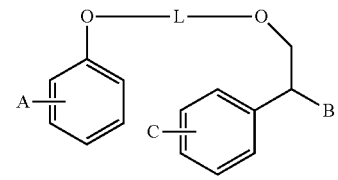

wherein L is selected from the group consisting of

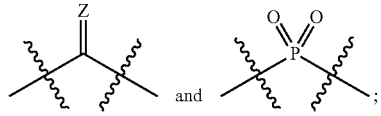

Z=O, S or NR7, R7=H, alkyl, aryl, —OH, —O, or a lower alkoxy; A is aryl, heteroaryl, fused pyran, or a fused tetrahydropyran; B is C(=O)—O—R6; R6 is an alkaloid azabicyclo ring substituent; C is H, F, lower alkoxy, CN, S(O)nCH3, where n=0-2, and Z=O.

Another embodiment provides a compound selected from the group consisting of:

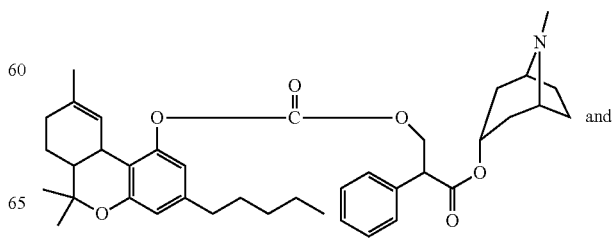

and

-continued

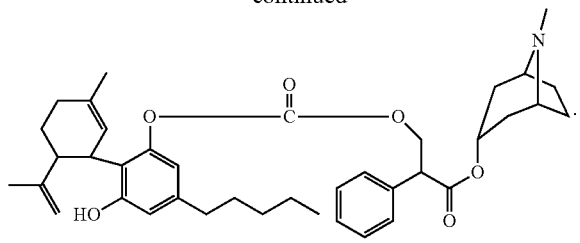

In another embodiment such compounds may be administered to a subject in need in effective doses corresponding to the therapeutic doses of THC, CBD and/or atropine. The composition of the present invention may be used to treat symptoms associated with OP or carbamate exposure. Such symptoms include ocular symptoms, skeletal motor symptoms, respiratory and CNS associated symptoms. In another embodiment, the ocular symptoms to be treated include lacrimal gland stimulation (tearing), painful pupillary sphincter contraction (miosis), and ciliary body spasm (ocular pain). In another embodiment, the respiratory symptoms being treated include dyspnea, bronchospasm, coughing, rhinorrhea, bronchorhea, respiratory distress, sensation of shortness of breath, respiratory failure, pulmonary edema, and air hunger. The gastrointestinal symptoms that ensue after exposure usually include hyper salivation, vomiting, diarrhea, and stomach cramps.

In another embodiment, the symptoms being treated include motor symptoms such as fasiculations, dyskinesia, akinesia, tremor, bradykinesia, skeletal muscle rigidity, and spasticity. In yet another embodiment, the CNS symptoms being treated include cognitive brain damage, neuropathy including axonopathy, anxiety, memory impairment, PTSD, and depression.

In at least one aspect of the present invention, the composition of the present claims may be administered either directly or indirectly to the site of interest by way of eye drop, eye ointment, oral spray, rectal suppository, intravenously, intramuscularly, subcutaneously, intradermally, orally in the form of capsules or tablets or diluted oils, topical rubs on the skin or mucous membrane, or buccally. Alternatively, the formulation may be applied directly to the site of interest such as via nasal application devices to sphenopalatine ganglion and cribriform plate, which is the pathway to the olfactory cranial nerve and brain, as well as the cerebrospinal fluid or by way of inhalation of vapors for rapid absorption. In the alternative, the formulation may also be introduced as a vapor into a gas mask, bag/valve mask used in manual resuscitation or assisted breathing, nasal cannulation, CPAP, or Continuous Positive Airway Pressure or variants of CPAP such as BiPAP, or via intubation with or without general anesthesia. Other objects, features, benefits and advantages of the present invention will be apparent from this summary and the following descriptions of certain embodiments, and will be readily apparent to those skilled in the art having knowledge of various chemotherapeutic compounds, methods and/or modes of operation.

BRIEF DESCRIPTION OF THE FIGURES

FIG. 1A depicts the composition of the inventive terpene blends described herein FIG. 1B depicts the composition of the inventive terpene blends described herein.

DETAILED DESCRIPTION OF THE INVENTION

Unless defined otherwise, all technical and scientific terms used herein have the same meanings as are commonly understood by one of skill in the art to which this invention belongs and shall be understood to have the meanings described below. All publications and patents referred to herein are incorporated by reference in their entirety. Unless otherwise specified, a reference to a particular compound includes all such isomeric forms, including racemic and other mixtures thereof. Unless otherwise specified, a reference to a particular compound also includes ionic, salt, solvate (e.g., hydrate), protected forms, prodrugs, and other stereoisomers thereof, for example, as discussed herein.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

The term "lower alkoxy" is defined as $C_1$ to $C_3$ alkoxy.

The term "benzodiazepine" as used herein pertains to all different short and long acting benzodiazepines, including but not limited to prodrugs, as well as estazolam, flurazepam, temazepam, triazolam, alprazolam, chlordiazepoxide, clorazepate, diazepam, halazepam, lorazepam, midazolam, oxazepam, prazepam, quazepam, and clonazepam. Benzodiazepine antagonists are thus such compounds that antagonize the benzodiazepine activities, especially respiratory depression secondary to benzodiazepine toxicity.

The term "cannabinoid" as used herein pertains to all different cannabinoids that have been isolated from the Cannabis sativa plant or synthetically created to have activity involving the endocannabinoid system. The term cannabinoid includes, but are not limited to, all classes of cannabinoids from Cannabis derived from cannabigerol-type compounds, including (9THC), cannabidiol (CBD), cannabinol (CBN), and dodeca-E, 4E,8Z,10E/Z-tetraenoic-acid-isobutylamides, cannabigerol (CBG), cannabichromene, cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethylether (CBGM).

As used herein, the term "composition" is intended to encompass a product comprising the specified ingredients in the specified amounts, as well as any product which results, directly or indirectly, from combination of the specified ingredients in the specified amounts.

The term "organophosphate" as used herein, pertains to compounds that are generally esters, amides, or thiol derivatives of phosphoric, phosphonic, or phosphinic acids. Aside from certain limited medical uses, these compounds are typically used as insecticides, pesticides, petroleum additives, and even warfare nerve agents. Organophosphates include substances such as echothiophate, diisopropyl fluorophosphate (DFP), tabun, GA, GB (sarin), GD, GF, VX, VE, VG, VM, diazinon, malathion, and parathion.

The term "terpenes" or "terpenoids" as used herein refers to a class of hydrocarbon occurring volatile molecules that provide a unique smell. Terpenes are derived from units of isoprene, which has the molecular formula $C_5H_8$. The basic molecular formulae of terpenes are multiples of that, $(C_5H_8)_n$ where n is the number of linked isoprene units. They include but are not limited to limonene, beta-caryophyllene, myrcene, linalool, pinene, terpineol, and terpinolene, and any isomeric forms thereof.

The term "treatment" or "therapy" as used herein in the context of treating a condition, pertains generally to treatment and therapy of a human subject, in which some desired therapeutic effect is achieved. For example, therapy can include the inhibition of the progress of the condition, reduction in the rate of progress, a halt in the rate of progress, amelioration of the condition, absolute or partial prevention of a delayed complication, and cure of the condition. Treatment also includes prophylactic measure as well as adjunct treatments to a standard treatment regimen established in the art.

The term "therapeutically-effective amount," as used herein, pertains to that amount of an active compound, or a material, composition or dosage form comprising an active compound, which is effective for producing some desired therapeutic effect, commensurate with a reasonable benefit/risk ratio.

It may be convenient or desirable to prepare, purify, and/or handle the active compound in the form of a prodrug. The term "prodrug" as used herein, pertains to a compound which, when metabolized, yields the desired active compound or in itself is the active compound. Typically, the prodrug is inactive, or less active than the active compound, but may provide advantageous handling, administration, or metabolic properties. For example, some prodrugs are ethers or esters of the active compound; during metabolism the ether group is cleaved to yield the active drug. Also, some prodrugs are activated enzymatically to yield the active compound, or a compound which, upon further chemical reaction, yields the active compound. Thus, in the methods of treatment of the present invention disclosed herein, the term "administering" shall encompass the treatment of the various conditions described with the compound specifically disclosed or with a compound which may not be specifically disclosed, but which converts to the specified compound in vivo after administration to the patient. Metabolites of these compounds include active species produced upon introduction of compounds of this invention into the mammalian subject.

Any of the compounds of the present invention may be contemplated for administration to the human subject in the form of a drug, prodrug or even active metabolite.

The cannabinoid and the THC-CBD combinations have been known in the art for treating or preventing a number of diseases or disorders. For example, U.S. Pat. No. 6,630,507 discloses cannabinoids for use as anti-oxidants and neuroprotectants; U.S. Pat. No. 7,105,685 discloses Cannabinoids for the treatment of diseases associated with immune dysfunction, particularly HIV disease and neoplastic disorders; U.S. Pat. No. 7,109,245 discloses Cannabinoids useful as vasoconstrictors; US Patent Publication US20110257256 discloses THC-CBD composition for use in treating or preventing Cognitive Impairment and Dementia; PCT Publication WO/2009/147439 discloses use of a combination of THC and CBD in the manufacture of a medicament for use in the treatment of cancer, in particular the glioma tumor (a brain cancer); PCT Publication WO/2007/148094 discloses use of THC-CBD composition for the treatment of neuropathic pain; and US Patent Publication US20100286098 discloses a method of treating tissue injury in a patient with colitis administering the THC-CBD combination.

Currently, US Drug Enforcement Administration (DEA) lists cannabis as a Schedule 1 compound which means *Cannabis* and similarly scheduled cannabinoids have not been shown to have safety and/or accepted medical use. However, different combinations of cannabinoids are still under investigation.

The psychoactive constituent in cannabis, 9THC, was isolated in the period 1963-64 by Prof. Raphael Mechoulam, but the cannabinoid receptors, the CB1 and the CB2, and the preliminary endogenous cannabinoids, e.g., anandamide and 2-arachidonoyl glycerol, were identified only 20 to 25 years later. The cannabinoid system affects both central nervous system (CNS) and peripheral processes. In at least one aspect of the invention, methods of manufacturing a pharmaceutical composition containing a cannabinoid is contemplated, including the steps of purifying and/or isolating the cannabinoid receptor agonist and mixing said agonist with a pharmaceutically acceptable carrier.

In one aspect of the present invention, methods of ameliorating or treating a cannabinoid receptor mediated disease, disorder or syndrome in a human subject are disclosed by such steps as administering to the subject an effective amount of a composition containing cannabinoid receptor modifiers and/or terpenes such as d-limonene, pinene, myrcene, linalool, beta caryophylene, or a combination thereof.

More particularly, the present invention relates to a method of treating OP or carbamate related toxicity in human patients. In this aspect of the invention, methods are provided for modulating the CB system to reduce functional signs or toxicity following exposure to OP or carbamate. In such a method, patients receive a therapeutically effective amount of EC system modulator for sufficient time to reduce the time of acetylcholine binding to its respective receptors thereby limiting cholinergic signs of toxicity associated with prolonged OP exposure.

In at least one embodiment, the mediated disease, disorder, dysfunction or syndrome being treated is secondary to organophosphate exposure and includes appetite disorder (such as loss of appetite), muscle disorder, ophthalmic dysfunction, metabolic disorders, cardiac, rhythm and contractility dysfunctions, social related disorders, mood disorders, seizures, substance abuse, learning disorders, cognition disorders, memory disorders, respiratory disorders, locomotor activity disorders, movement disorders, immune disorders, inflammation, cell growth, pain or neurodegenerative related syndromes, substance abuse including alcohol abuse, bipolar disorder, cognitive impairment, post-traumatic stress disorder (PSTD), Gulf War syndrome type disorders, and premature senile dementia. In a preferred embodiment, the instantly described methodology is used as an adjunctive treatment to the standard medical regimen typically used for OP toxicity.

In another embodiment, the muscle disorders are dyskinesia, akinesia, tremor, bradykinesia, and skeletal muscle rigidity and spasticity. In another embodiment the ophthalmic disorders are miosis, ciliary muscle spasm, ophthalmic pain, headache and lacrimation disorder.

In yet another embodiment, the present invention is directed to methods of antagonizing G and V class nerve agent organophosphate toxicity via administering to a subject in need thereof a cannabinoid receptor agonist, its free base, or in pharmaceutically acceptable salt form and a pharmaceutically acceptable carrier. Such toxicities include those that lead to permanently cognitive impairment, such as attention deficit disorder, executive function disorder, loss of coordination particularly when operating hazardous machinery, learning disability, safe driving, and delayed axonopathy.

In a preferred embodiment, the present invention is directed to a synergistic combination of suitable cannabinoid, terpene and an alkaloid such as atropine. In this embodiment, such combination can be in a water soluble solution, suspension, or other suitable delivery system, or in a kit. In another embodiment, any such ingredients may be linked together by way of a biodegradable linker system releasing individual active ingredients.

In another embodiment, the present invention provides a synergistic combination of a CB receptor agonist, or partial agonist with a secondary pain medication including but not limited to opioids, NSAIDS, gabapentin, pregabalin, a benzodiazepine, atropine, oxime, antioxidants (e.g., grape seed, blueberry extracts, vitamin E, and vitamin C), and suitable alkalizing agents.

The present invention discloses the novel uses of cannabinoid receptor modifiers in the treatment of the symptoms associated with the OP exposure. By way of example, cannabinoid receptor agonists employed in the present invention include, but are not limited to, delta 9THC, CBD, CBN, nabilone, dronabinol, nabiximols, or mixtures thereof. Cannabinoid receptor antagonists include rimonabant.

In another aspect of the present invention, endogenous ligands of the cannabinoid receptors, such as anandamide and 2-AG, and endocannabinoid metabolizers diacylglycerol lipase (DAGL) and degradation of these lipid mediators (fatty acid amide hydrolase (FAAH) and MAGL (monoacylglycerol lipase)) are formulated in combination with cannabinoid receptor modifiers such as 9THC, CBD, CBD-V, THC-V, CBN, nabilone, dronabinol, nabiximols, and rimonabant. In a more preferred embodiment, the combination comprises at least any two of 2-AG, DAGL, 9THC, CBD, CBN, nabilone, dronabinol, Epidiolex®, nabiximols, and rimonabant. Other minor lipid metabolites different from, but chemically similar to, anandamide and 2-AG are also suitable for the presently described formulations.

In at least another embodiment, the invention manipulates the endocannabinoid system, a G-protein-coupled cannabinoid receptor to treat symptoms associated with the OP toxicity. In the brain, endocannabinoid primarily influences neuronal synaptic communication and affects biological functions, including eating, anxiety, learning and memory, reproduction, metabolism, growth and development, via an array of actions throughout the nervous system. In at least one aspect of the present invention, EC signaling function is targeted to improve the therapeutic benefits of cannabinoids and terpenes in protecting subjects at risk due to carbamate or OP exposure. In another aspect of the present invention, the agonists used to activate or selectively block one type of cannabinoid receptor more potently than the other type partial agonists or full agonists with differing CB1 and CB2 receptor affinities.

In another aspect, the present invention is the new discovery of the correlation of desirable properties of CB agonists and supplemental terpenes in alleviating the symptoms of toxic OP or carbamate exposure. In a preferred embodiment, such properties include pupillary dilatation or at least a decrease in miosis and recovery to normal size, dry eyes, dry mouth, muscle relaxation, neuroprotection against oxidative stress, and anxiolysis. In other word, those of ordinary skill in the art would appreciate that the undesirable properties of recreationally smoking marijuana causes, i.e., dry eyes, dilated pupils, dry mouth, reduced ability to vomit if one desires to vomit, and difficulty with micturition are shown herein to be serendipitous benefits, desirably prevent, decrease or provide therapeutic effects in the context of OP and carbamate toxicity. Those of ordinary skill in the art can further appreciate that the ideal property sought in cananbinoid therapy is devoid of unwanted psychoactive components, or attempts to minimize them in a risk: benefit assessment, except for perhaps an anxiolytic effect and reduction in memory of being acutely sick from OP or carbamate intoxication.

It is also well established that CB1 receptors are widespread in the brain which can explain its involvement in multiple memory stages that might require different neural substrates. In this context, several intriguing reports suggest the presence of CB1 receptors in astrocytes. See Navarrete M., Araque A. 2010. Endocannabinoids potentiate synaptic transmission through stimulation of astrocytes. See Neuron 68, 113-126) and mitochondria (Benard G., et al. 2012. Mitochondrial CB1 receptors regulate neuronal energy metabolism. Nat. Neurosci. 15, 558-56), where they can also participate in the control of cognitive processes.

In the brain, cannabinoids and endocannabinoids modulate a number of intracellular signaling pathways, some critically involved in the deleterious effect of cannabinoids on learning and memory processes. The involvement of the mammalian target of the rapamycin pathway and extracellular signal-regulated kinases, together with their consequent regulation of cellular processes such as protein translation, seem to play a critical role in the amnesic-like effect of cannabinoids. In at least one embodiment, methods of limiting brain toxicity and cognitive impairment associated with OP exposure are disclosed. In such methods, cannabinoids are directly and locally administered to brain regions identified to be at risk secondary to OP toxicity. Mode of administration in this aspect of the invention includes suitably designed nasal and/or regional catheters.

In at least one embodiment of the present invention, CB agonists can be administered locally, that is cutaneously, over areas of skin sweating and fasiculations and directly to the site(s) of interest such as via nasal applicators to the sphenopalatine ganglion and cribiform plate or by way of inhalation for rapid absorption. In another embodiment, the CB agonists are administered ophthalmically and buccally in the form of an isotonic solution, extracts, ointments, inhaler or injectable. In another embodiment, a water soluble delivery system is administered by inhalation via an electric charge e-cigarette or a nebulizer.

In a preferred embodiment, the formulation contains a sufficient amount of cannabinoid to competitively inhibit the binding of OP to the AChE. In at least one embodiment the formulation contains 27 mg of 9THC and at least 25 mg of CBD, COG or CADGE in alkyl alcohol. In a more preferred embodiment, the formulation comprises 1-3 mg of (−)-delta-9THC and 25 mg CBD, wherein each 100 microliter spray for sublingual delivery contains up to 0.05 g alcohol.

In another embodiment, at least a composition containing a terpene mixture is described. In such embodiment, terpenes may be a combination of limonene:pinene:myrcene:linalool:beta caryophylene:terpineol:terpinolene in such ratios as 1-10:1-10:1-6:1-6:0.25-3:0-10:0-10, respectively. In another embodiment, the ratio between such terpenes is 4:4:3:3:1:0:0. In yet another embodiment, the ratio between such terpenes is respectively 4:7:3:3:2:0:0.

In another embodiment, other ingredients can be used to formulate a stable cannabinoid, terpene, and alkaloid composition. Such ingredients include but are not limited to Sterile Water, Organic Vegetable Glycerine, phospholipids, glycerols, polyethylene glycerol, or volatile acid to formulate a *Cannabis* extract having a concentration of 15-50 mg of cannabinoids per ml, and 5% alcohol (for preservation). In another aspect of the invention, the cannabinoids may be present and mixed with Grapeseed Oil with an organic solvent such as alcohol ranging from 0-5% w/v.

In a more preferred embodiment such formulation can be applied for a maximum of 25 sprays per day with at least a 15-minute gap between sprays. In another embodiment, such formulation is applied for a total of 15 sprays per week.

In another embodiment, the CB agonist is administered orally. At least one suitable drug is nabilone, a synthetic cannabinoid. Nabilone occurs as a white to off-white polymorphic crystalline powder. In aqueous media, the solubility of nabilone is less than 0.5 mg/L, with pH values ranging from 1.2 to 7.0. Chemically, nabilone (±)-trans-3-(1,1-dimethylheptyl)-6,6a,7,8,10,10a-hexahydro-1-hydroxy-6,6-dimethyl is similar to the active ingredient found in naturally occurring 9THC. In at least one embodiment, nabilone can be administered orally at doses ranging from 0.005 mg to 200 mg, preferably 1 mg to 100 mg in a tablet, capsule, oral solution, immediate or extended release formulations. In a more preferred embodiment nabilone is administered orally at 0.05, 0.5, 1, or 2 mg and two to three times a day.

In another aspect of the present invention, those of ordinary skill in the art would appreciate that the present invention establishes the link between antagonizing specific and general manifestation activities of the chemical war nerve agents of the G and V classes as well as toxicity secondary to OP or carbamate insecticide exposure in humans. In at least one embodiment, the formulation containing the CB agonist or modulator is administered in the form of an eye drop or ointment. In this aspect of the invention, the eye drop may be used to prevent or minimize miosis and/or ciliary muscle spasm and/or lacrimation secondary to G and V agent or carbamate exposure.

In another aspect of the invention, the CB receptor agonist can be an active metabolite of THC. In another embodiment, the CB agonist or modifier can be administered intranasally to the sphenopalatine ganglion and cribiform plate regions of the patient with or without atropine, with or without a decongestant, or with or without a local anesthetic. In a more preferred embodiment, this mode of administration is accomplished by a long-acting local anesthetic ingredient. As used herein, the CB modifiers include such compounds that can compete with endocannabinoids or can enhance agonistic activities at such receptor sites.

In another aspect of the invention, the CB receptor agonist is administered via inhalation to mucosal membranes and alveoli of the respiratory tract via the mouth or nose. In this aspect of the invention, the agonist may also be administered via vaporization, or a nebulization via a mask nebulizer, below the temperature of combustion so as to be less irritating to mucosal and alveoli of the respiratory tract via the mouth or nose. In another embodiment, the cannabinoid may be delivered to the alveoli as well as to the sphenopalatine ganglion, olfactory nerve, and cribiform plate.

In yet another embodiment, the cannabinoid formulation is administered by inhalation, via nose and/or via mouth in the form of a nanomolar formulation or a liposomal formulation that includes added terpenes and/or atropine dry powder via suitable metered dose inhaler, or an electronic nebulizer, designed to deliver therapeutically effective amount of the agonist to the lung. In a more preferred embodiment, the CB receptor agonist is in dry powders or liposomes having particles size diameters ranging from 10 nanometers to 3000 nm, preferably ranging from 50 nm to 2000 nm. In a more preferred embodiment, the liposomes have a wall containing phosphatidylcholine, phosphatidic acid, cholesterol and phosphatidylethanolamine.

In another aspect of the invention, the CB receptor agonist is prepared in the form of a culinary extract in the form of or resembling butter or margarine to be used for baking and cooking. In another embodiment, the product is in a form ready for vaporization such as in an E cigarette, or administration into a gas mask, bag/valve mask or CPAP device, or any form combining cannabinoids with or without added terpenes, but optionally with atropine, an oxime and/or a benzodiazepine for combination therapy. In a preferred embodiment, the potent anticholinergic drug combination includes a cannabinoid modulator with or without terpenes in combination with atropine, oxime and a benzodiazepine.

In certain embodiments of the present invention a composition containing the CB agonist or a modifier can further contain a pharmaceutically-acceptable carrier component. Without limitation, such a composition can comprise a racemic mixture of compounds.

In another embodiment, the invention relates to a method for use in treating or preventing ophthalmic pain, muscular spasticity, neuromuscular pain, including neuropathic pain secondary to OP or carbamate toxicity. In a more preferred embodiment, the preferred combination product is used as an adjunctive therapy to standard OP or carbamate toxicity medical management.

In at least one aspect of the invention, the inventor discloses formulations containing cannabinoid that are used to alleviate or prevent brain injuries that can be caused by prolonged OP or carbamate exposure causing increased cholinergic tone. It has been shown that within the hippocampus at least, cannabinoids presynaptically inhibit the release of acetylcholine, possibly through the activation of CB 1 receptors located on cholinergic nerve terminals. Direct in vivo microdialysis studies in rats also showed cannabinoid-induced decreases in acetylcholine release in the hippocampus through a CB 1 receptor-mediated mechanism. In at least one aspect of the present invention, the cannabinoid compositions are used for Prevention/treatment/mitigation of OP or carbamate induced brain injuries.

In this aspect of the invention, the pharmaceutical composition is in oral, nasal, topical, ophthalmic, buccal, sublingual, rectal, vaginal, vapor, and/or parenteral form.

The above active compounds may also be used as part of an in vitro assay, for example, in order to determine whether a candidate host is likely to benefit from treatment with the compound in question. Any active compound of the present invention may also be used as a standard, for example, in an assay, in order to identify other active compounds, other anti-proliferative agents, other anti-inflammatory agents, etc.

In yet another aspect of the instant invention, the IC50 or the half maximal inhibitory concentration of the candidate compounds were determined to assess drug potency and potential dosing regimens for in vivo use. One of ordinary skill in the art is readily able to ascertain such information using commonly known methodologies. As it has been well described in the art, IC50 represents and measures how much of a particular substance/molecule is needed to inhibit some biological process by 50%. In the instant case, the IC50 of the candidate compounds were determined as the concentration that led to a response of 50% compared to the vehicle control cells.

As noted herein, the salts of the compounds of this invention refer to non-toxic "pharmaceutically acceptable salts." Other salts may, however, be useful in the preparation of the compounds according to the invention or of their pharmaceutically acceptable salts. When the compounds of the present invention contain a basic group, salts encompassed within the term "pharmaceutically acceptable salts" refer to non-toxic salts which are generally prepared by reacting the free base with a suitable organic or inorganic acid. Representative salts include any such salt known in the art. Where compounds of the present invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

To treat a human patient, an effective amount of one or more compounds of the present invention, or a pharmaceutically-acceptable salt thereof, is administered to the human subject in need so as to promote exposure to or contact of the tissue at risk or the targeted region of the body or nerves, synapses, or neuromuscular junctions, or organ systems including but not limited to the autonomic and central nervous systems. Effective dosage forms, modes of administration and dosage amounts may be determined empirically, and making such determinations is within the skill of the art.

It is understood by the physician, pharmacists or clinician of ordinary skill in the art that the dosage amount will vary with the activity of the particular compound employed, course and/or progression of the disease state, the route of administration, the rate of excretion of the compound, status of the nervous system, renal and hepatic function of the patient, the duration of the treatment, the identity of any other drugs being administered to the subject, age, weight and like factors.

As discussed herein, the cannabinoid compounds of the present invention can be administered in such oral dosage forms as tablets, capsules (each of which includes sustained release or timed release formulations), pills, powders, micronized compositions, granules, elixirs, tinctures, suspensions, ointments, vapors, liposomal particles, nanoparticles, syrups and emulsions. Likewise, they may also be administered in intravenous (bolus or infusion), intraperitoneal, topical (e.g., dermal epidermal, transdermal, ophthalmically such as ocular eyedrop, intranasally, subcutaneous, inhalation, intramuscular or transdermal (e.g., patch) form, all using forms well known to those of ordinary skill in the pharmaceutical arts. Again, the ordinarily skilled physician, veterinarian or clinician or a clinical pharmacist may readily determine and prescribe the effective amount of the drug required to prevent, counter or arrest the progress of the condition.

Dosages of phytocannabinoids, e.g., THC and CBD, or synthetics of the present invention, when used for the indicated effects, will range between about 0.0001 mg per kg of body weight per day (mg/kg/day) to about 100 mg/kg/day, preferably 0.001 to 20 mg/kg/day, and most preferably 0.01 to 10.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously or via a vapor inhalation, the most preferred doses will range from about 0.01 to about 10 mg/kg/minute during a constant rate infusion or rate of respiration. Compounds of the present invention may be administered in a single daily dose, or the total daily dosage may be administered in divided doses of two, three or four or six times daily. In the case of a prodrug construct, those of ordinary skill in the art would appreciate that the clinical outcome follows the same serum concentrations or clinical endpoints as those of THC or CBD.

In at least one embodiment, the method of treatment includes both prophylactic and active treatment regimens. In at least one such embodiment, the suitable composition contains a blend of CBD to THC having the ratio of CBD:THC in ranges of 10-400 mg:0.0001-10 mg. In yet another embodiment, such method includes the step of administering a blend of terpenes optionally including pinene. In a more preferred embodiment, pinene may be added in case there is exposure to oxime. This is because pinene has a beneficial bronchodilatorory effects to counteract OP or carbamate induced bronchospasm. However, pinene also has an anticholinesterase property. This property would make pinene more ideal as a prophylactic and less ideal as a post-exposure therapeutic unless an oxime and atropine are administered shortly after OP or toxic carbamate exposure. THC also has an anticholinesterase property that makes it useful for prophylaxis only in microgram quantities. THC is likewise less ideal as a post-exposure therapeutic in other than microgram quantities unless an oxime and atropine are administered shortly after OP or toxic carbamate exposure In another embodiment, the method is intended for active treatment of emotional and neurophysiological stresses, involuntary eye muscles twitches, bronchospasm, fasiculations, tremors, seizures, headaches, neuropathy and neuropsychiatric disorders including PTSD. In yet another embodiment, prophylactic methods are contemplated to counter OP toxicity. Accordingly, such methods include the step of sniffing a terpene mixture, wherein the terprene mixture contains a terpene blend of limonene, myrcene, linalool, beta caryophylene, terpineol, terpinolene optional pinene, and mixtures thereof.

As noted herein, the compounds of the present invention may be used in combination with other pain management, anticholinergic agents or other agents which will enhance the treatment regime for the human subjects. The individual components of such combinations can be administered separately at different times during the course of therapy or concurrently in divided or single combination forms to patients or regions of such patients in need of such therapy. The instant invention is therefore to be understood as embracing all such regimes of simultaneous or alternating treatment and the term "administering" is to be interpreted accordingly. It will be understood that the scope of combinations of the compounds of this invention with other agents useful to treat the targeted cancer condition includes in principle any combination with any pharmaceutical composition useful for treating disorders related to optimal cholinergic and general nervous system functioning.

Pharmaceutical formulations of the present invention include those suitable for oral, nasal, topical (including buccal and sublingual), rectal, vaginal and/or parenteral administration. Regardless of the route of administration selected, the active ingredient(s) are formulated into herbal and pharmaceutically-acceptable dosage forms by conventional methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

In another aspect of the invention, a cannabinoid formulation is described to prevent unauthorized diversion of a formulation that contains clinically significant amounts of THC or other CB1 agonist with psychoactive properties. As such the formulation agonist with psychoactive activity may have atropine or a similar anticholinergic agent added. The anticholinergic property of atropine, in the absence of OP or carbamate, will cause an uncomfortably dry mouth and dryness at other mucous membranes. Approved medications that contain atropine (or pharmacologically similar belladonna alkaloids) to prevent diversion of a narcotic or barbiturate, respectively, and/or to aid in intended therapeutic activity include for diarrhea diphenoxylate/atropine and for spastic colon, phenobarbital with hyoscyamine, atropine and scopolamine. Spastic colon is also called IBS, or Irritable Bowel Syndrome. IBS is a symptom-based diagnosis characterized by chronic abnormal pain, discomfort, bloating, and alteration of bowel habits. As a functional GI disorder, IBS has no known organic causes diarrhea or constipation may predominate, or they may alternate (classified as IBS-D, IBS-C or IBS-A, respectively).

Another aspect of the present invention provides compounds having the following structure:

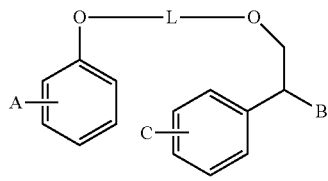

In such embodiment, L is a linker bridging a cannabinoid moiety to an alkaloid moiety. In a preferred embodiment, L is

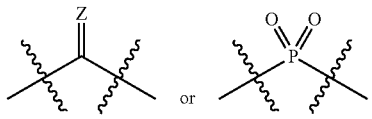

attached at the designated points, Z=O, S, or NR7, and where R7=H, alkyl, aryl, —OH, or —O—C1-C3 alkyl.

In a more preferred embodiment, A is aryl, heteroaryl, fused pyran, or fused tetrahydropyran; B is C(=O)—O—R6, where R6 is an azabicyclo ring substituent (alkaloid); and C is H, F, or C1-C3 alkoxy, CN, or S(O)$_n$CH$_3$, where n=0-2, and Z=O. Methods of preparing such compounds generally follow the conventional methods known in the art.

In at least one embodiment, Z is O (a carboxy group linker), and the new compound has the formula:

i

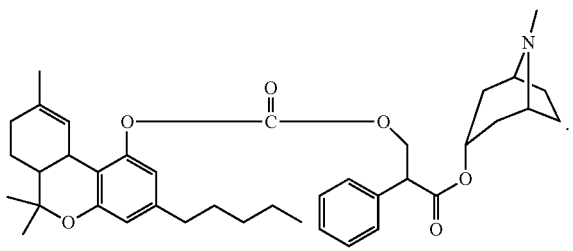

THC/atropine construct

-continued ii

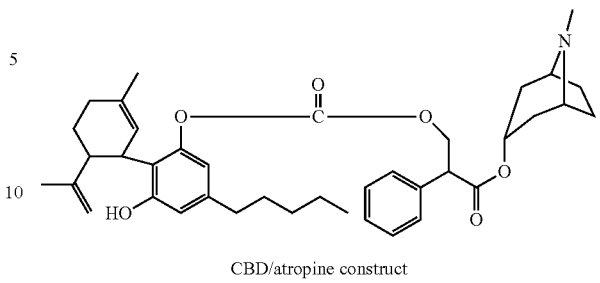

CBD/atropine construct

Methods of preparing compounds are understood in the art and follow those employing carboxylate, phosphate and amine moieties. Methods of preparing formulations or compositions include the step of bringing the active ingredient(s) into association with the carrier and, optionally, one or more accessory and/or stabilizing or preserving ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup or tincture, or as pastilles (using an inert base, such as gelatin and glycerin, or sucrose and acacia) and/or as mouth washes and the like, each containing a predetermined amount of the active ingredient(s). The active ingredient(s) may also be administered as a bolus, electuary or paste.

In solid dosage forms of the invention for oral administration (capsules, tablets, pills, dragees, powders, granules and the like), the prodrug(s), active ingredient(s) (in their micronized form) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl-cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using a binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres or nanoparticles. They may be sterilized by, for example, filtration through a bacteria-retaining filter. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl acetate, butyl alcohol, benzyl benzoate, propylene glycol, glycol, oils (in particular, cottonseed, groundnut, corn, germ, olive, castor, hempseed, cocoanut, and sesame oils), terpenes or terpinoids, glycerol or glycerol, amyl alcohol, tetrahydrofuryl polyethylene glycols and fatty acid esters of sorbitan, and mixtures thereof.

Besides inert diluents the oral compositions may also include wetting agents, emulsifying and suspending agents, sweetening, flavoring, coloring, perfuming and preservative agents. Suspensions, in addition to the active ingredient(s), may contain suspending agents as, for example, ethoxylated alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredient(s) with one or more suitable nonirritating excipients or carriers comprising, for example, cocoa butter, polyethylene glycol, wax or salicylate which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate.

Dosage forms for the topical, ophthalmic or transdermal administration of the active ingredient(s) include powders sprays, ointments, pastes, creams, lotions, gels, solutions, patches and inhalants. The active ingredient(s) may be mixed under sterile conditions with pharmaceutically-acceptable carrier, and with any buffers, or propellants which may be required.

The ointments, pastes, creams and gels may contain, in addition to the active ingredient(s), excipients, such as animal and vegetable fats, oils, waxes, paraffins, starch, tragacanth, cellulose derivatives, polyethylene glycols, silicones, bentonites, silicic acid, talc and zinc oxide, terpenes or terpinoids, or mixtures thereof. Powders and sprays can contain, in addition to the active ingredient(s), excipients such as lactose, talc, silicic acid, aluminum hydroxide, calcium silicates and polyamide powder, or mixtures of these substances. Sprays can additionally contain customary propellants such as chlorofluorohydrocarbons and volatile unsubstituted hydrocarbons, such as butane and propane.

Compounds of the present invention may be administered in intranasal form via topical use of suitable intranasal vehicles, or via transdermal routes, using those forms of transdermal skin patches well known to those of ordinary skill in the art. A transdermal delivery system provides for continuous administration throughout the dosage regimen. Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers, such as iontophoresis, can also be used to increase the flux of the active ingredient(s) across the skin or a mucous membrane or a mucocutaneous junction area. The rate of such flux can be controlled by either providing a rate-controlling membrane or dispersing the active ingredient(s) in a polymer matrix or gel.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamines or phosphatidylcholines.

Another mode of delivery for the compounds of the present invention may be delivery via the use of monoclonal antibodies as individual carriers to which the compound molecules are coupled. The compounds of the present invention may also be coupled with soluble polymers as targetable drug carriers. Such polymers can include polyvinylpyrrolidone, yeast derivatives (e.g., glucans), pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydro gels.

Pharmaceutical compositions of this invention suitable for parenteral administration comprise the active ingredient(s) in combination with one or more pharmaceutically-acceptable sterile isotonic aqueous or nonaqueous solutions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and non-aqueous carriers which may be employed in the formulation. In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form. Alternatively, delayed absorption of parenterally-administered active ingredient(s) is accomplished by dissolving or suspending the active ingredient(s) in an oil vehicle.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly (orthoesters) and poly(anhydrides). Depot injectable formulations are also prepared by entrapping the active ingredient(s) in liposomes or microemulsion or nanoparticles which are compatible with body tissue. The injectable materials can be sterilized for example, by filtration through a bacterial-retaining filter.

The formulations may be presented in unit-dose or multi-dose sealed containers, for example, ampoules and vials, or in specialized capsules for vapor or nebulized administration and may be stored in a lyophilized condition requiring only the addition of the sterile liquid carrier, for example water or oil for injection, immediately prior to use. Extemporaneous injection solutions and suspensions maybe prepared from sterile powders, granules and tablets of the type described above.

Unless otherwise specified all starting materials and reagents are of standard commercial or medicinal grade, and are used without further purification, or are readily prepared from such materials by routine methods. Those skilled in the art of clinical therapeutics will recognize that starting materials and reaction conditions may be varied to achieve the desired end product. In at least one embodiment, a kit is described containing differing prophylactic and active treatment regimen for a cannabinoid rescue regimen.

Figure 1B:
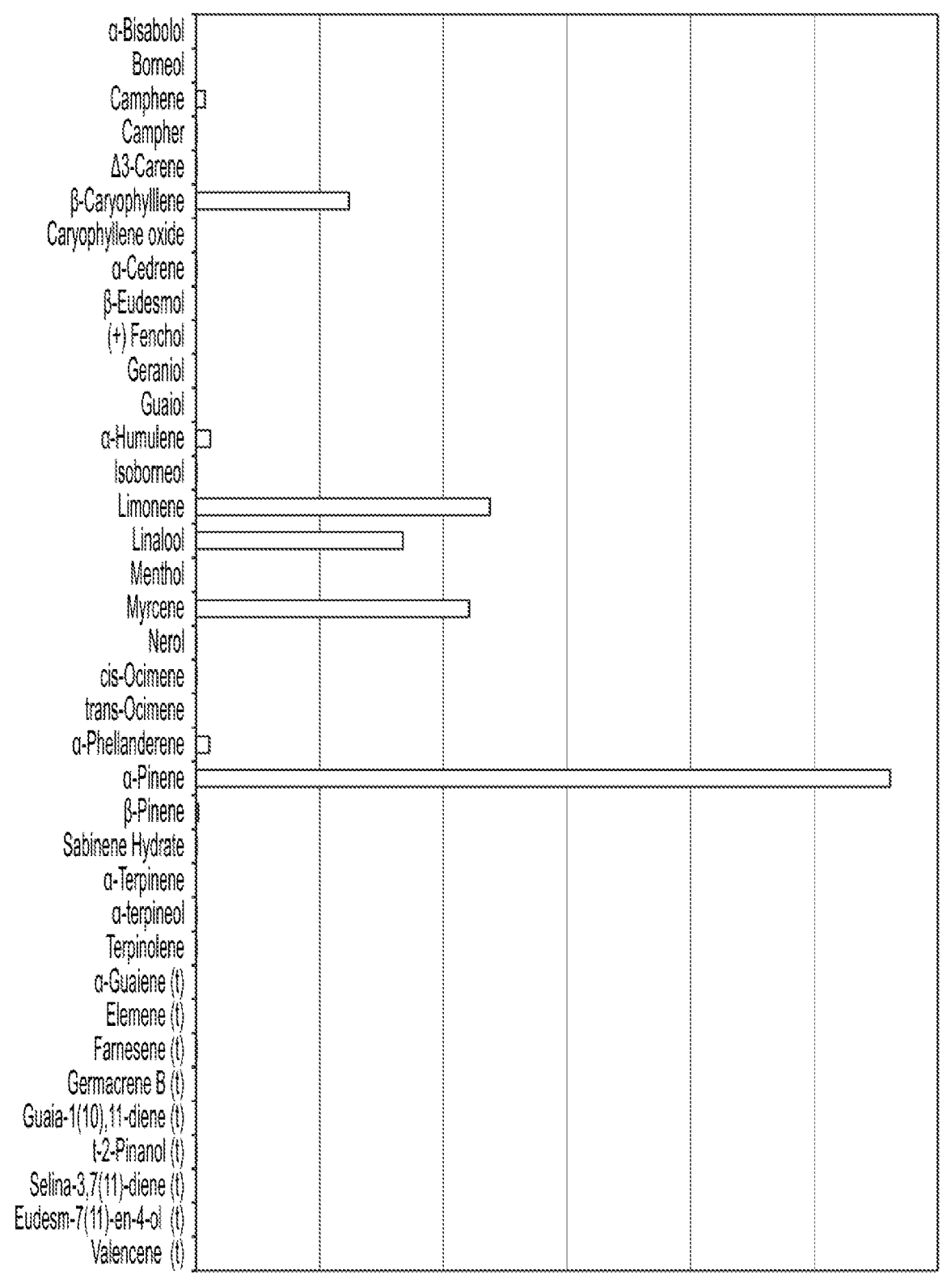

In this aspect of the invention, the cannabinoid therapy may include a terpene blend containing limonene, alpha pinene, myrcene, linalool and beta carylophylene preferably in weight ratios of about 4:7:3:3:2. (See FIG. 1). In another embodiment such prophylactic kit contains CBD containing compositions for both inhalation therapy and oral administration. In another embodiment, the therapy or the terpene blend may contain THC in amounts less than 1 mg.

In another aspect of the invention, the cannabinoid rescue regimen is a kit for active treatment. In addition to the terpene blend and CBD composition, the active treatment kit contains THC:CBD containing compositions in the ratios of 1:10, 1:12.5, 1:15, 1:20, and 1:40 w/w. Such kit may further contain hemp oil, atropine, an oxime, a benzodiazepine, instructions as to the order of treatment and other administration means. In a more preferred embodiment, the THC:CBD composition and terpenes are water soluble. In another preferred embodiment, the atropine/oxime is lipid soluble.

The following examples are meant to better define the scope of the present invention.

Example 1

OP toxicity was determined using DFP toxicity. Male and female albino rats (total 4 rats) were singly dosed subcutaneously with different amounts of the DFP. Severity of salivation, lacrimation, urination and defecation (SLUD) signs were measured at dose levels of 0.63, 1.88, 1.25, and 2.5 DFP mg/kg. Dose escalation is used if the previous doses used do not, induce sufficient responses to test efficacy of the test article such as abnormal pupil response, SLUD, arousal, abnormal motor movement, gait and posture.

Example 2

The same protocol as in Example 1 is conducted in a primate to measure the OP DFP toxicity by monitoring the same parameters to find a dose level that would provide clear and measureable evidence of DFP toxicity in a primate.

Example 3

In order to test the onset of cannabinoid and terpene activities in rats, a combination of THC, CBD, and terpenes were administered to the animals. In accordance with an IRB approved protocol, a first group of rats were administered a terpene blend for 20 seconds of sniffing of the blend. After sniffing of the terpene blend, different combinations of cannabinoids by themselves or in cannabinoid/terpene blends were administered by oral gavage.

At least one of the blend combinations was composed of D-limonene:alpha pinene:myrcene, linalool:beta caryophylene in volumetric ratios of about 4:4:3:3:1 respectively to make approximately a 30 mg/kg dose. The same method may be used to explore other combinations within the scope of the ratios described herein above, such as for example, a terpene blend containing limonene, alpha pinene, myrcene, linalool and beta carylophylene preferably in weight ratios of about 4:7:3:3:2 as described in FIG. 1.

In another experiment the animals are given THC at doses of 0.001, 0.01, 0.05, 0.1, 0.5, 1, and high doses of 2.5 or 3 mg/kg. Another group of the animals are given a mixture containing CBD:THC at CBD doses including but not limited to 0.1, 1, 10, 12.5, 15, 20, 25, 30, 37.5 mg/kg and such THC doses to make up ratios of 10:1, 12.5:1, or 15:1, 20:1, 25:1, 40:1, 100:1, and 200:1 CBD:THC respectively.

In another experiment the animals are given CBD at doses of 0.25, 1, 5, 50, 75, 100, 150, and 200 mg/kg and a terpene blend at a dose of 40 mg/kg-120 mg/kg.

In another experiment the animals are given THC at 2.5 mg/kg, CBD at 15 mg/kg and terpene blend at 40 mg/kg. In another experiment the animals are given an undiluted terpene blend via sniffing for 2 seconds. Then the THC/CBD/terpene blend was administered by oral gavage 2.25 hours prior to subcutaneous administration of DFP.

Observations: Female rats tolerate higher doses of DFP than male rats. Cannabinoid effects such as hyperthermia, abnormal gait and posture seen with both THC and CBD receiving animals, particularly more prominent at 8 hours than at 4 hours after dosing, showing splayed hind limbs and hunched or crouched body position. Both DFP and cannabinoids cause significant hypothermia in rats, (but not in primates). All animals receiving cannabinoids with and without additional terpenes or just a terpene blend recovered at 24 hours after receiving the test materials. Terpenes by themselves appeared very well tolerated, except the rats did not like the smell of linalool. The degree of hypothermia observed with groups receiving CBD was unexpected, potentially due to questionable integrity of CBD formulation. CBD is expected to attenuate hypothermia associated with THC in rats.

Example 4

Animals were tested for efficacy of the cannabinoid rescue therapy. In the first study, 4 male and 4 female Sprauge Dawley rat pups were treated initially with DFP subcutaneously at dose of 1.35 mg/kg for males and 1.9 mg/kg for females. A Cannabinoid mixture was delivered by oral gavage at 2.25 hours prior to the administration of DFP and again 24 hours later. Animals could then sniff terpene blend for 2 seconds immediately prior to gavage and again the terpene alpha pinene for 2 seconds prior to first DFP subcutaneous injection. Similar approach may be taken in other species, however, cannabinoids and terpenes may be administered as vapors or in ways other than oral gavage.

An outcome of at least 10%, improvement in toxicity parameters is to be observed in animals, such as primates who received THC, CBD and terpenes prophylactically. Small doses of atropine/oxime will be available as soon as possible after exposure vs. conventional therapy of only atropine/oxime. These improvement changes are less likely to be seen in rodents due to biological differences in reactions to cannabinoids. Related parameters in other systems would indicate at least a 10% overall improvement in all other major organ systems impacted by DFP or another OP.

For example, animals receiving the treatment regimen would show at least a 10% less abnormal respiratory rate, hypoxemia, audible wheeze, digital pulse oximetry abnormalities, abnormalities in FEV1 (forced expiratory volume) at one (1) second and vital capacity as well as any flow volume loop measurable by spirometry. In the alternative, respiratory distress assessments based on pulse oximetry and/or arterial blood gas analysis including $CO_2$ retention as compared to non-treatment group. Similarly, animals receiving the cannabinoid rescue regimen will exhibit substantial clinical response to supplemental oxygen in part due to reduced bronchospasm and respiratory hyper secretion (bronchorhinorhea).

Neuropsychiatric exam will also show at least 10% less disorientation and learning abnormalities or measures of cognitive function at 30 days after moderate to severe OP exposure (following at least a 3-day washout from any significant dose of THC or a CB 1 receptor agonist). Similar results would be observed for parameters indicative of axonopathy from delayed OP-induced neuropathy. Other clinical signs related to the severity of PTSD, severity of anxiety, depression are to be monitored in appropriate interval respectively associated with development of abnormal signs in the animal models. Those of ordinary skill in the art can appreciate that a proper approach would implement a washout period after psychoactive cannabinoid administration before any memory assessments or cognitive task assessments could be determined.

Neuromuscular exam will also provide for at least a 10% decrease in severity of tremors, other abnormal movements, and a 20% decrease in seizures. In a preferred outcome, at least a 20% decrease in LD 50 studies is observed in primates in groups that have received prophylactically alpha pinene and low dose THC and CBD where concentrations of CBD to THC follows at least a 20:1 ratio respectively.

In an alternative regimen, the treatment plans include (a) CBD with or without a terpene blend and optionally (b) atropine or oxime or both following OP exposure.

At least one aspect of the present invention describes improvements that would include at least 10% improvements in hypersalivation and eye pain, clinically significant SLUD, dryness and other cholinergic adverse effects as compared with a prophylactic pyridostigmine bromide treatment. It is contemplated that in primates cannabinoid therapy results in a more rapid return of pupil size from the miosis induced by an OP or a carbamate. OP-induced miosis from G class nerve agent vapors that reach the eye is resistant to treatment with atropine.

In another observation, neuroprotective effect from cannabinoids as an adjunct to standard therapy will be superior to standard therapy alone 30 days after exposure and when assessed against a standalone pyridostigmine treatment.

In yet another embodiment, high CBD:THC (>20:1) ratios, with or without terpenes but if with terpenes then without significant pinene would provide an alternative standard treatment in cases where atropine and an oxime will not be administered in a timely fashion. This approach may be suitable particularly for civilian use.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as claimed in the appending claims.

All publications, patents, and patent applications cited in this application are herein incorporated by reference to the same extent as if each individual publication, patent, or patent application was specifically and individually indicated to be incorporated herein by reference.

I claim:

1. A method for treating symptoms caused by exposure to sarin or aldicarb comprising:
   (i) administering a composition comprising tetrahydrocannabinol (THC) and cannabidiol (CBD) to a subject exposed to sarin or aldicarb, wherein the THC and CBD are in a therapeutically-effective amount to treat the symptoms, wherein the administration of the THC/CBD composition is oral, nasal, buccal, sublingual, or parenteral; and
   (ii) optionally administering a composition of linalool and beta-caryophyllene; wherein the administration of the linalool is via a gas mask.

2. The method of claim 1 wherein the ratio of THC:CBD is about 1:10 to about 1:40.

3. The method of claim 1 wherein the amount of THC is about 0.0001 mg to about 10 mg and the amount of CBD is about 3 mg to about 400 mg.

4. The method of claim 1 wherein step (ii) is required and linalool and beta-caryophyllene are in a ratio of from 6:0.25 to 1:3.

5. The method of claim 1 wherein step (ii) is required and linalool and beta-caryophyllene are in a ratio of 3:1.

6. The method of claim 1 wherein step (ii) is required and linalool and beta-caryophyllene are in a ratio of 3:2.

7. The method of claim 1 further comprising administering a non-cannabinoid active ingredient estazolam.

8. The method of claim 1, further comprising administering flurazepam.

9. The method of claim 1 wherein the THC is (6aR,10aR)-6,6,9-trimethyl-3-pentyl-6a,7,8,10a-tetrahydrobenzo[c]chromen-1-ol.

10. The method of claim 1 wherein the administration of the THC/CBD composition is parenteral.

11. The method of claim 10 wherein the parenteral administration of the THC/CBD composition is an intramuscular injection.

12. The method of claim 10 wherein the parenteral administration of the THC/CBD composition is an intravenous injection.

13. The method of claim 1 wherein the THC/CBD composition is administered orally.

14. The method of claim 1 wherein the THC/CBD composition is administered sublingually.

15. The method of claim 1 wherein the THC/CBD composition is administered buccally.

16. The method of claim 1 wherein the THC/CBD composition is administered nasally.

17. The method of claim 1 wherein step (ii) is required and the administration of the linalool and beta-caryophyllene is via a gas mask.

18. The method of claim 1, wherein step (ii) is required.

* * * * *